United States Patent
Hossainy et al.

(10) Patent No.: US 6,783,793 B1
(45) Date of Patent: Aug. 31, 2004

(54) SELECTIVE COATING OF MEDICAL DEVICES

(75) Inventors: Syed F. A. Hossainy, Fremont, CA (US); Daryush Mirzaee, Sunnyvale, CA (US)

(73) Assignee: Advanced Cardiovascular Systems, Inc., Santa Clara, CA (US)

(*) Notice: Subject to any disclaimer, the term of this patent is extended or adjusted under 35 U.S.C. 154(b) by 0 days.

(21) Appl. No.: 09/697,106

(22) Filed: Oct. 26, 2000

(51) Int. Cl.$^7$ ............................ B05D 3/00; A61F 2/06
(52) U.S. Cl. ................. 427/2.25; 623/1.46; 623/11.11; 427/2.24
(58) Field of Search .......................... 623/11.11, 1.42, 623/1.46; 604/96; 427/2.24, 2.25, 2.3, 2.1, 2.28

(56) References Cited

U.S. PATENT DOCUMENTS

| | | | |
|---|---|---|---|
| 4,489,670 A | 12/1984 | Mosser et al. | 118/55 |
| 4,616,593 A | 10/1986 | Kawamura et al. | 118/303 |
| 5,342,621 A | 8/1994 | Eury | 424/423 |
| 5,443,496 A | 8/1995 | Schwartz et al. | 623/1 |
| 5,464,650 A | 11/1995 | Berg et al. | 427/2.3 |
| 5,538,493 A | 7/1996 | Gerken et al. | 494/16 |
| 5,605,696 A | 2/1997 | Eury et al. | 424/423 |
| 5,624,411 A | 4/1997 | Tuch | 604/265 |
| 5,637,113 A | 6/1997 | Tartaglia et al. | 623/1 |
| 5,649,977 A | 7/1997 | Campbell | 623/1 |
| 5,656,082 A | 8/1997 | Takatsuki et al. | 118/52 |
| 5,700,286 A | 12/1997 | Tartaglia et al. | 623/1 |
| 5,707,385 A | 1/1998 | Williams | 606/192 |
| 5,843,172 A | 12/1998 | Yan | 623/1 |
| 5,897,911 A | 4/1999 | Loeffler | 427/2.25 |
| 5,968,091 A * | 10/1999 | Pinchuk et al. | 623/11.11 |
| 5,980,972 A | 11/1999 | Ding | 427/2.24 |
| 6,013,099 A * | 1/2000 | Dinh et al. | 623/11.11 |
| 6,042,875 A * | 3/2000 | Ding et al. | 427/2.24 |
| 6,056,993 A * | 5/2000 | Leidner et al. | 427/2.25 |
| 6,140,127 A * | 10/2000 | Sprague | 435/395 |
| 6,153,252 A * | 11/2000 | Hossainy et al. | 427/2.3 |
| 6,203,551 B1 * | 3/2001 | Wu | 606/108 |
| 6,517,889 B1 * | 2/2003 | Jayaraman | 427/2.24 |
| 6,555,157 B1 * | 4/2003 | Hossainy | 427/2.24 |
| 6,562,136 B1 | 5/2003 | Chappa et al. | 118/500 |
| 6,605,154 B1 | 8/2003 | Villareal | 118/500 |

FOREIGN PATENT DOCUMENTS

| | | | |
|---|---|---|---|
| EP | 0 627 226 | 12/1994 | |
| EP | 0 850 651 | 7/1998 | |
| WO | WO 01/52772 A1 * | 7/2001 | ............. A61F/2/06 |
| WO | WO 01/91918 | 12/2001 | |

OTHER PUBLICATIONS

Syed F. A. Hossainy and Jeffrey Steward, inventors; USSN 09/625,070 filed Jul. 25, 2000, entitled "Method for Coating and Implantable Device and System for Performing the Method".

* cited by examiner

Primary Examiner—Corrine McDermott
Assistant Examiner—Javier G. Blanco
(74) Attorney, Agent, or Firm—Squire, Sanders & Dempsey, LLP (57) ABSTRACT

Methods for coating different regions of an implantable device are disclosed. An embodiment of the method includes dipping a first portion of the implantable device into a first coating substance, and then centrifuging the implantable device to provide an even coating. Next, a second portion of the implantable device is dipped into a second coating substance, and the implantable device is again centrifuged, resulting in an even second coating. In another embodiment, a first coating substance is applied to an interior surface of a cylindrical implantable device, such as a tent or graft, and a second coating substance is applied to an exterior surface. A centrifuge step is performed so that the first coating substance is preferentially and uniformly applied on the interior surface of the implantable device and the second coating substance is preferentially and uniformly applied on the exterior surface of the implantable device.

30 Claims, 3 Drawing Sheets

SELECTIVE COATING OF MEDICAL DEVICES

FIELD OF THE INVENTION

The present invention relates to the coating of an implantable device. More specifically, this invention relates to a method for selective coating of an intraluminal implantable device, such as a stent or graft.

BACKGROUND

Occlusion of blood vessels reduces or blocks blood flow. During the course of atherosclerosis, for example, growths called plaques develop on the inner walls of the arteries and narrow the bore of the vessels. An emboli, or a moving clot, is more likely to become trapped in a vessel that has been narrowed by plaques. Further, plaques are common sites of thrombus formation. Together, these events increase the risk of heart attacks and strokes.

Traditionally, critically stenosed atherosclerotic vessels have been treated with bypass surgery in which veins removed from the legs, or small arteries removed from the thoracic cavity, are implanted in the affected area to provide alternate routes of blood circulation. More recently, implantable devices, such as synthetic vascular grafts and stents, have been used to treat diseased blood vessels.

Synthetic vascular grafts are macro-porous vessel-like configurations typically made of expanded polytetrafluoroethylene (ePTFE), polyethylene terephthalate (PET), polyurethane (PU), or an absorbable polymer. Grafts made of ePTFE or PET are very non-wetting materials when introduced into an aqueous environment, causing difficulty in impregnating the materials. In addition, grafts made of ePTFE or PET typically are permanently implanted in the body, while grafts made of an absorbable polymer bioabsorb over time. A graft may be positioned into the host blood vessel as a replacement for a diseased or occluded segment that has been removed. Alternatively, a graft may be sutured to the host vessel at each end so as to form a bypass conduit around a diseased or occluded segment of the host vessel.

Percutaneous transluminal coronary angioplasty (PTCA) is a procedure for treating heart disease in which a catheter assembly having a balloon portion is introduced percutaneously into the cardiovascular system of a patient via the brachial or femoral artery. The catheter assembly is advanced through the coronary vasculature until the balloon portion is positioned across the occlusive lesion. Once in position across the lesion, the balloon is inflated to a predetermined size to radially compress against the atherosclerotic plaque of the lesion to remodel the vessel. The balloon is then deflated to a smaller profile to allow the catheter to be withdrawn from the patient's vasculature.

Restenosis of the artery commonly develops over several months after the procedure, which may require another angioplasty procedure or a surgical by-pass operation. Restenosis is thought to involve the body's natural healing process. Angioplasty or other vascular procedures injure the vessel walls, removing the vascular endothelium, disturbing the tunica intima, and causing the death of medial smooth muscle cells. Excessive neoinitimal tissue formation, characterized by smooth muscle cell migration and proliferation to the intima, follows the injury. Proliferation and migration of smooth muscle cells (SMC) from the media layer to the intima cause an excessive production of extra cellular matrices (ECM), which is believed to be one of the leading contributors to the development of restenosis. The extensive thickening of the tissues narrows the lumen of the blood vessel, constricting or blocking blood flow through the vessel.

Intravascular stents are sometimes implanted within vessels in an effort to maintain the patency thereof by preventing collapse and/or by impeding restenosis. Implantation of a stent is typically accomplished by mounting the stent on the expandable portion of a balloon catheter, maneuvering the catheter through the vasculature so as to position the stent at the desired location within the body lumen, and inflating the balloon to expand the stent so as to engage the lumen wall. The stent maintains its expanded configuration, allowing the balloon to be deflated and the catheter removed to complete the implantation procedure. A covered stent, in which a graft-like covering is slip-fit onto the stent, may be employed to isolate the brittle plaque from direct contact with the stent, which is rigid.

To reduce the chance of the development of restenosis, therapeutic substances may be administered to the treatment site. For example, anticoagulant and antiplatelet agents are commonly used to inhibit the development of restenosis. In order to provide an efficacious concentration to the target site, systemic administration of such medication may be used, which often produces adverse or toxic side effects for the patient. Local delivery is a desirable method of treatment, in that smaller total levels of medication are administered in comparison to systemic dosages, but are concentrated at a specific site. Therefore, local delivery may produce fewer side effects and achieve more effective results.

One commonly applied technique for the local delivery of a therapeutic substance is through the use of a medicated implantable device, such as a stent or graft. Because of the mechanical strength needed to properly support vessel walls, stents are typically constructed of metallic materials. The metallic stent may be coated with a polymeric carrier, which is impregnated with a therapeutic agent. The polymeric carrier allows for a sustained delivery of the therapeutic agent.

Various approaches have previously been used to join polymers to metallic stents, including dipping and spraying processes. In one technique, the stent is first formed in a flat sheet, placed in a solution of polyurethane, and heated for a short period of time. Additional polyurethane solution is applied on top of the flat sheet, and the stent is again heated. This process produces a polyurethane film over the surface of the stent, and excess film is manually trimmed away. In one variation of this technique, microcapsules containing therapeutic agents are incorporated into the polyurethane film by adding the microcapsules to the polyurethane solution before heating.

In another technique, a solution is prepared that includes a solvent, a polymer dissolved in the solvent, and a therapeutic agent dispersed in the solvent. The solution is applied to the stent by spraying the solution onto the stent using an airbrush. After each layer is applied, the solvent is allowed to evaporate, thereby leaving on the stent surface a coating of the polymer and the therapeutic substance. Use of this spraying technique to apply a thick coating may result in coating uniformity problems, so multiple application steps are sometimes used in an attempt to provide better coating uniformity.

In yet another coating technique, a solution of dexamethasone in acetone is prepared, and an airbrush is used to spray short bursts of the solution onto a rotating wire stent. The acetone quickly evaporates, leaving a coating of dexamethasone on the surface of the stent.

The above-described methods often have difficulty in applying an even coating on the stent surfaces. One common result when using these spraying or immersion processes is that the aqueous coating tends to collect in crevices, apertures, or cavities in the framework of the stent, resulting in an uneven coating having an uncontrollably variable coating thickness. In particular, an excess amount of coating is often entrained in the angle between two intersecting struts of a stent, which is sometimes called "webbing" or "pooling." The deposition of excessive amounts of therapeutic agents results in a poor surface area to volume ratio relative to conformal coatings. When such a coating experiences uncontrolled drying, drying artifacts may result in drug crystal formation.

The use of multiple applications of a fine, diffuse spray may produce a more controllable, even coating than immersion techniques. However, the diffuse application results in much of the coating substance not coating the stent and instead being released into the air. This inefficient use of the coating substance wastes the coating substance, which may be quite expensive, and increases the exposure of the air brush operator to the coating substance.

In addition, existing methods for coating implantable devices do not provide effective techniques for applying coatings of different substances onto different portions of the surface of the implantable device.

SUMMARY

In view of the above, there is a need to provide an improved method for coating medical devices which produces superior coating uniformity and control of the location of the coating without an excessive loss of materials. It is also desirable that the coating method can be used on a variety of implantable devices with aqueous or solvent-based coating substances. In particular, it is desired that therapeutic or bioactive substances, such as compositions of a polymer, solvent, and therapeutic substance, can be used to coat stents.

In accordance with various aspects of the present invention, the invention relates to a method for coating an implantable device. In one embodiment, the method comprises applying a first coating substance on a first portion of a surface of the implantable device, applying a second coating substance on a second portion of a surface of the implantable device, and rotating the implantable device about an axis of rotation. In another embodiment, a first coating substance is applied to an interior surface of a cylindrical implantable device, such as a stent or graft, and a second coating substance is applied to an exterior surface. A centrifuge step is performed so that the first coating substance is preferentially and uniformly applied on the interior surface of the implantable device and the second coating substance is preferentially and uniformly applied on the exterior surface of the implantable device.

Various embodiments of the described method enable highly viscous materials to be coated onto implantable devices. Viscous materials are not usually amenable to conventional coating methods such as dipping or spraying, because of the viscous material's propensity to accumulate in an uneven layer. However, the addition of a centrifugation step after dipping the implantable device in the viscous coating material can transform the uneven masses into a smooth, even coating.

Embodiments of the method also enable uniform coatings to be applied to implantable devices with improved repeatability, thereby improving coating uniformity between batches of implantable devices. With conventional manually-applied spray-coating techniques, operator error or inconsistency may result in different coating thicknesses between batches of stents. The centrifugation processes can reduce unwanted gross deposition of coating substances and enable high reproducibility of the coating quality.

Embodiments of the method also enable multiple stents to be processed simultaneously. Unlike manually-applied airbrush coating methods, in which stents are coated individually or in small groups, large batches of stents can be simultaneously immersed in the coating solution, simultaneously rotated in the centrifuge device, and simultaneously heated in an oven, thereby increasing throughput.

Embodiments of the method also may improve operator safety when coating implantable devices with hazardous materials. It is generally not desirable to spray coat an implantable device with toxic or radioactive coating substances, because of the increased exposure of the operator to the airborne hazardous coating substance. Dipping and centrifuging the implantable device as described above can decrease the amount of handling required for the coating process, resulting in reduced environmental contamination.

Embodiments of the method may also mitigate defects due to handling of the implantable device. In conventional spray processes, the implantable device is held aloft using one or two clamps or fixtures while the coating substance is sprayed onto the device. The point where these clamps contact the device may be masked from receiving the spray, resulting in defects in the coating. In contrast, the centrifuge container has minimal contact with the implantable device during the centrifuge process.

In another embodiment of the present invention, the invention relates to a drug loaded implantable device comprising two or more coating substances, each of the substances applied to portions of the device. In one embodiment, the portions are exterior surfaces of the device. In yet another embodiment, one of the portions is an exterior surface and another of the portions is an interior surface of the device. Further, one of the substances applied to the device can be a first substance that evenly coats a first portion of the device. Another of the substances can be a second substance that evenly coats a second portion of the device.

BRIEF DESCRIPTION OF THE DRAWINGS

The features of the described embodiments are specifically set forth in the appended claims. However, embodiments relating to both structure and method of operation are best understood by referring to the following description and accompanying drawings, in which similar parts are identified by like reference numerals.

DETAILED DESCRIPTION

The following description is meant to be illustrative only and not limiting. Other embodiments of this invention will be apparent to those of ordinary skill in the art in view of this description.

The figures generally illustrate the techniques used to apply coatings to a stent in accordance with an embodiment of the present invention. Although the illustrated and described embodiments may relate to wire-based stents, any of a variety of implantable devices may be subjected to the coating process described herein, including, but not limited to, wire-based stents, tubular stents, rolled-sheet type stents, stent coverings, vascular grafts, or any implantable device having a complicated architecture which is not amenable to standard coating.

The materials from which such stents are formed may include metals such as, but not limited to, stainless steel, "MP35N," "MP20N," elastinite (Nitinol), tantalum, nickel-titanium alloy, platinum-iridium alloy, gold, magnesium, or combinations thereof. "MP35N" and "MP20N" are trade names for alloys of cobalt, nickel, chromium and molybdenum available from standard Press Steel Co., Jenkintown, Pa. "MP35N" consists of 35% cobalt, 35% nickel, 20% chromium, and 10% molybdenum. "MP20N" consists of 50% cobalt, 20% nickel, 20% chromium, and 10% molybdenum. The stent also may be made from virtually any biocompatible material, such as bioabsorbable or biostable polymers.

Vascular grafts may be used to replace, bypass, or reinforce diseased or damaged sections of a vein or artery. These grafts can be made from any suitable material including, but not limited to, highly open-pored materials such as polymers of expanded polytetrafluoroethylene (ePTFE) and polyethylene terephthalate (PET), or less porous materials such as polyurethanes, absorbable polymers, and combinations or variations thereof. Grafts may be formed using a lyophilization process. Polyurethanes from which the graft may be made include, but are not limited to, Biomer, BioSpan® polyurethane (manufactured by Polymer Technology Group, Berkeley, Calif.; referenced herein after as "BioSpan®"), and Elastion. Absorbable polymers from which the graft may be made include, but are not limited to, polycaprolactone (PCL), poly(lactic acid) (PLA), poly(glycolic acid) (PGA), polyanhydrides, polyorthoesters, polyphosphazenes, and components of extracellular matrix (ECM). In such an embodiment, additional interstices can be formed in the graft by any conventional methods known to one of ordinary skill in the art, including exposure of the graft to a laser discharge to form a pattern of pores.

In other embodiments, the implantable device to be coated is a covering for a self-expandable or balloon-expandable stent. This covering can be formed of materials similar to those from which the above-described graft may be formed.

Various types of coating substances may be applied to an implantable device in accordance with the present invention. In one embodiment, the coating substance includes a polymer loaded with a therapeutic substance. The terms "polymer," "poly," and "polymeric" as used herein mean the product of a polymerization reaction and are inclusive of homopolymers, copolymers, terpolymers, etc., whether natural or synthetic, including random, alternating, block, graft, crosslinked, blends, compositions of blends and variations thereof. The term "pre-polymer" refers to a low molecular weight material, such as oligomers, that can be further polymerized regardless of the mechanism of polymerization.

The polymer or combination of polymers can be applied to a stent based on the polymer's or polymers ability to carry and release, at a controlled rate, various therapeutic agents such as antithrombogenic or anti-proliferative drugs. The polymeric material is most suitably biocompatible, including polymers that are non-toxic, non-inflammatory, chemically inert, and substantially non-immunogenic in the applied amounts. The polymer is typically either bioabsorbable or biostable. A bioabsorbable polymer breaks down in the body and is not present sufficiently long after implantation to cause an adverse local response. Bioabsorbable polymers are gradually absorbed or eliminated by the body by hydrolysis, metabolic process, bulk erosion, or surface erosion. Examples of bioabsorbable materials include but are not limited to polycaprolactone (PCL), poly-D, L-lactic acid (DL-PLA), poly-L-lactic acid (L-PLA), poly(lactide-co-glycolide), poly(hydroxybutyrate), poly(hydroxybutyrate-covalerate), polydioxanone, polyorthoester, polyanhydride, poly(glycolic acid), poly(glycolic acid-cotrimethylene carbonate), polyphosphoester, polyphosphoester urethane, poly (amino acids), cyanoacrylates, poly(trimethylene carbonate), poly (iminocarbonate), copoly(etheresters), polyalkylene oxalates, polyphosphazenes, polyiminocarbonates, and aliphatic polycarbonates. Biomolecules such as heparin, fibrin, fibrinogen, cellulose, starch, and collagen are typically also suitable. Examples of biostable polymers include Parylene® and Parylast® (available from Advanced Surface Technology of Billerica, Mass.), polyurethane, such as a segmented polyurethane solution containing a dimethylacetamide (DMAc) solvent developed by the Polymer Technology Group, Inc. of Berkeley, Calif., and known by the trade name BioSpan® polyethylene, polyethlyene teraphthalate, ethylene vinyl acetate, silicone and polyethylene oxide (PEO).

The expression "therapeutic agent" as used herein broadly refers to an agent or substance including, but not limited to, a therapeutic substance, a polymer impregnated with therapeutic substance, radioactive isotope, and radiopaque material, that possesses desirable therapeutic characteristics. The therapeutic agent may be, for example, antineoplastic, antimitotic, antiinflammatory, antiplatelet, anticoagulant, antifibrin, antithrombin, antiproliferative, antibiotic, antioxidant, and antiallergic substances, as well as combinations thereof. Examples of such antineoplastics and/or antimitotics include paclitaxel (e.g., TAXOL® by Bristol-Myers Squibb Co., Stamford, Conn.), docetaxel (e.g., Taxotere® from Aventis S.A., Frankfurt, Germany) methotrexate, azathioprine, actinomycin-D, vincristine, vinblastine, fluorouracil, doxorubicin hydrochloride (e.g., Adriamycin® from Pharmacia & Upjohn, Peapack, N.J.), and mitomycin (e.g., Mutamycin® from Bristol-Myers Squibb Co., Stamford, Conn.). Examples of such antiplatelets, anticoagulants, antifibrin, and antithrombins include sodium heparin, low molecular weight heparins, heparinoids, hirudin, argatroban, forskolin, vapiprost, prostacyclin and prostacyclin analogues, dextran, D-phe-pro-arg-chloromethylketone (synthetic antithrombin), dipyridamole, glycoprotein IIb/IIIa platelet membrane receptor antagonist antibody, recombinant hirudin, and thrombin inhibitors such as Angiomax™ (Biogen, Inc., Cambridge, Mass.). Examples of such cytostatic or antiproliferative agents include angiopeptin, angiotensin converting enzyme inhibitors such as captopril (e.g., Capoten® and Capozide® from Bristol-Myers Squibb Co., Stamford, Conn.), cilazapril or lisinopril (e.g., Prinivil® and Prinzide® from Merck & Co., Inc., Whitehouse Station, N.J.); calcium channel blockers (such as nifedipine), colchicine, fibroblast growth factor (FGF) antagonists, fish oil (omega 3-fatty acid), histamine antagonists, lovastatin (an inhibitor of HMG-CoA reductase, a cholesterol lowering drug, brand name Mevacor® from Merck & Co., Inc., Whitehouse Station, N.J.), monoclonal antibodies (such as those specific for Platelet-Derived Growth Factor (PDGF) receptors), nitroprusside, phosphodiesterase inhibitors, prostaglandin inhibitors, suramin, serotonin blockers, steroids, thioprotease inhibitors, triazolopyrimidine (a PDGF antagonist), and nitric oxide. An example of an antiallergic agent is permirolast potassium. Other therapeutic substances or agents that may be used include alpha-interferon, Trapidil antiplatelet (manufactured by DAITO Corporation, Japan; referenced herein after as "Trapidil"), genetically engineered epithelial cells, and dexamethasone. In yet other embodiments, the therapeutic substance is a radioactive isotope used in radiotherapeutic procedures. Examples of radioactive isotopes include, but are not limited to, phosphoric acid ($H_3P^{32}O_4$), palladium ($Pd^{103}$), cesium ($Cs^{311}$), and iodine ($I^{125}$).

While the preventative and treatment properties of the foregoing therapeutic substances or agents are well known to those of ordinary skill in the art, the substances or agents are provided by way of example and are not meant to be limiting. Other therapeutic substances are equally applicable for use with the disclosed embodiments. For example, while many of the herein-described therapeutic agents have been used to prevent or treat restenosis, they are provided by way of example and are not meant to be limiting, since other drugs or coatings may be developed which are equally applicable for use with embodiment of the present invention.

In other embodiments, the coating is an aqueous solution of a therapeutic substance that does not contain a polymer matrix, for example, an aqueous solution of heparin. This aqueous solution can be applied to the stent and allowed to dry, thereby forming a heparin coating on the stent.

In addition to a polymer and a therapeutic agent, the coating substance may also include a solvent. The solvent can be virtually any solvent that is compatible with the implantable device to be coated. Examples of suitable solvents include but are not limited to dimethyl sulfoxide, dimethyl formamide, tetrahydrofuran, dimethyl acetamide, trichloroethane, acetone, ethanol, methanol, isopropanol, and ethyl acetate.

Figure 1:
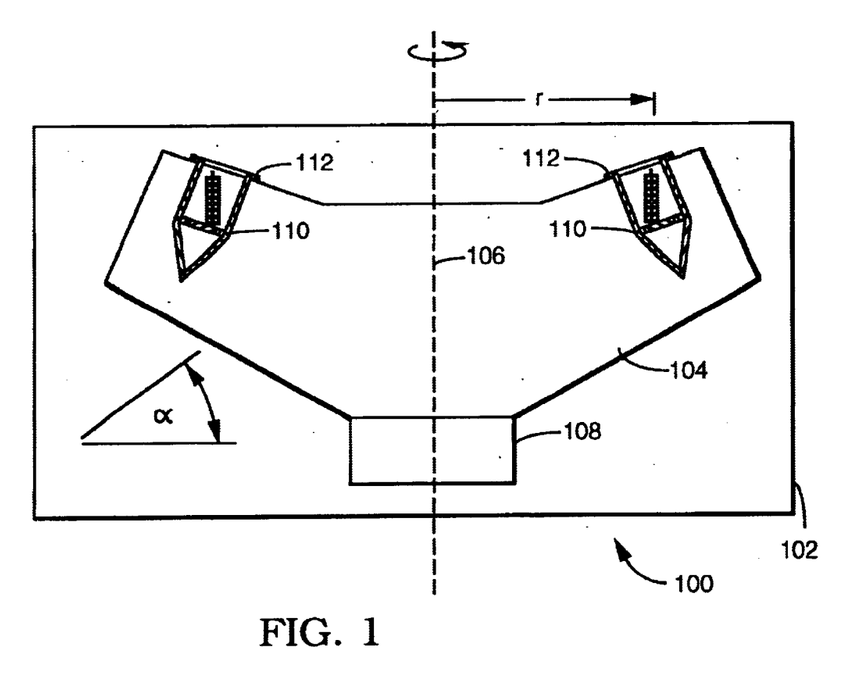
FIG. 1 illustrates in plan view a cross-section of an embodiment of a centrifuge system.

FIG. 1 shows a cross-section of an exemplary centrifuge system 100 in accordance with an embodiment of the present invention. Centrifuge system 100 includes a centrifuge device 102, which includes a rotatable rotor 104 for rotation about an axis 106, and a motor 108 which drives rotor 104 to rotate about axis 106. Centrifuge models 5410, 5415, 5417, 5804, and 5810, sold by Eppendorf Scientific, Inc., of Westbury, N.Y., may be used, for example, as centrifuge device 102. Exemplary centrifuge devices 102 provide rotational speeds of up to, for example, 14,000 rotations per minute ("RPM"). Rotor 104 includes a plurality of hollow chambers 110 circularly arranged about axis 106. Each chamber 110 is sized to receive a centrifuge container 112. Various centrifuge devices 102 available on the market are capable of centrifuging large numbers of centrifuge containers 112 simultaneously.

Figure 2:
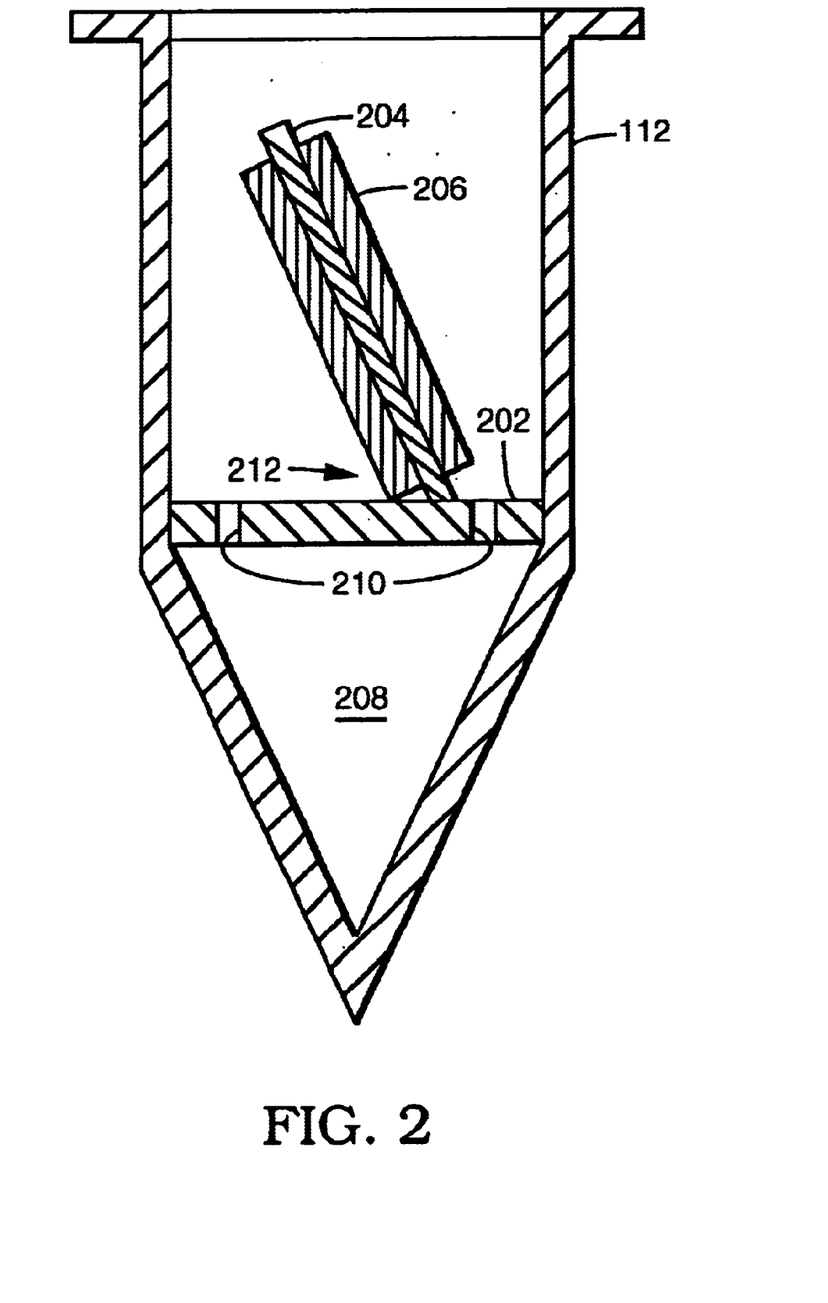
FIG. 2 is a cross-section in plan view of an embodiment of a centrifuge container.

FIG. 2 shows in greater detail a cross-section of an exemplary centrifuge container 112. Centrifuge container 112 can be formed using a conventional centrifuge tube that has been modified as described below. A support 202 is provided towards the bottom of centrifuge container 112, and a mandrel 204 is preferably mounted thereon. In this embodiment, mandrel 204 is a rod. Mandrel 204 is inserted into the interior of the implantable device to be coated, such as a cylindrical stent 206. Mandrel 204 holds stent 206 and prevents stent 206 from contacting the interior walls of centrifuge container 112. Support 202 separates stent 206 from runoff reservoir 208, which is provided at the bottom of centrifuge container 112. Drainage openings 210 may be provided in support 202.

As can be seen in the embodiment shown in FIGS. 1–2, mandrel 204 is tilted such that when each centrifuge container 112 is mounted in centrifuge system 100, stents 206 are positioned such that their longitudinal axes are nearly parallel to axis of rotation 106. This may provide a more even coating on stents 206 after centrifugation. In alternative embodiments, mandrels 204 may have a different tilt angle relative to the central axes of centrifuge containers 112, or may have no tilt at all.

Figure 3:
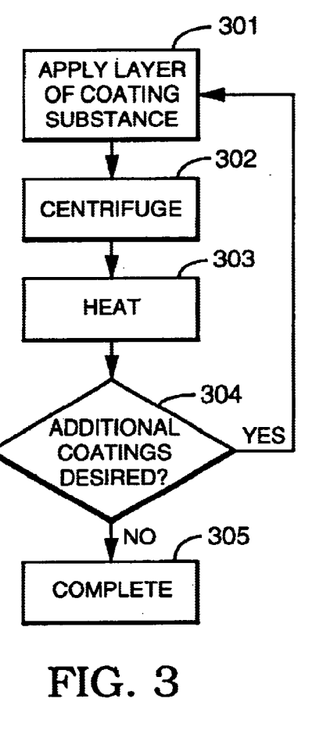
FIG. 3 is a flowchart of an embodiment of a coating process.
Figure 4:
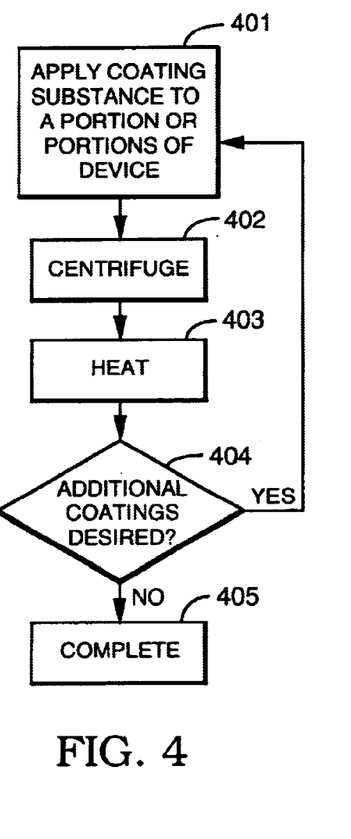
FIG. 4 is a flowchart of an alternate embodiment of a coating process.

FIGS. 3 and 4 are flowcharts illustrating exemplary methods of coating an implantable device in accordance with an embodiment of the present invention. For the sake of example, the implantable device described with respect to FIGS. 1–4 is a stent, but the method also may be applied to various other implantable devices discussed above.

Referring to FIG. 3, in act 301, a first coating is applied to stent 206. The coating may be applied by injecting, spraying or immersing stent 206 with a liquid coating substance using techniques similar to those described in the background section above. The term "liquid" as used herein refers to substances having sufficient fluidity such that the substance can flow over the surface of stent 206 when processed through the further acts described below. "Liquid" is not intended to limit the coating substance to water-based substances or to low viscosity materials. Even highly viscous substances such as a hyaluronic acid solution (e.g., 1% hyaluronic acid), high molecular weight polyethylene glycol solution, gelatin solution, or poly (lactic) acid in 1, 1, 2 trichloroethane (e.g., 10% poly (lactic) acid) are included within the term.

As occurs with conventional coating techniques, the spraying or immersion of stent 206 in the coating substance typically results in a non-uniform coating, with webbing being observable between struts on stent 206. The term "strut(s)" as used herein includes the elongated elements and interconnecting elements of stent 206. In act 302, the still-wet stent 206 is inserted onto mandrel 204 in centrifuge container 112 such that mandrel 204 extends through the hollow interior of stent 206. Centrifuge container 112 is then inserted into chamber 110 of centrifuge system 100 (FIG. 1), and centrifuge system 100 is used to rotate stent 206 about axis 106 at high speeds. Centrifuge system 100 includes a plurality of rotatable chambers 110, such that multiple coated stents 206 can be centrifuged simultaneously, thereby increasing processing throughput.

The rotation of chambers 110 at high speeds creates a centrifugal force upon the coating substance that previously was applied to the surface of stent 206. Centrifugal force causes excess accumulations of coating substance, particularly the portions entrained between the struts of stent 206, to evenly redistribute over stent 206. Redistribution of the coating substance over the surface of stent 206 provides a more uniform coating free of webbing.

The centrifugation of stent 206 may result in some excess coating substance being removed from the surface of stent 206. Drainage openings 210 are provided in support 202 so that the runoff coating substance can flow from the upper portion of centrifuge container 112 into runoff reservoir 208. The channeling of runoff coating substance into runoff reservoir 208 prevents the coating substance from accumulating at the bottom end 212 of stent 206, which could lead to a non-uniform coating. Runoff coating substance can be recovered from runoff reservoir 208 and reused to coat additional stents 206. The recycling of the coating substance can produce significant cost savings when an expensive therapeutic agent is being used.

In alternative embodiments, different structures are provided to effectuate the flow of runoff coating substance into runoff reservoir 208. In one embodiment, support 202 is square-shaped, such that when support 202 is fitted into a centrifuge container 112 which is cylindrical in shape, runoff coating substance can flow around the openings formed between the edges of square support 202 and the circular interior of centrifuge container 112. In another embodiment, support 202 comprises a mesh platform, such that fluid can freely flow through support 202 to pass into reservoir 208. Numerous other variations are possible.

In act 303, coated, centrifuged stent 206 is immediately placed into a conventional oven for heating. Heating evaporates solvents that might be present in the coating substance, thereby forming a solid coating on the surface of stent 206. Heating act 303 can improve the adhesion of the coating substance to the metal forming metallic stents 206, and can also provide a better equilibrium for the solid phase drug distribution in the matrix of the coating substance. Heating act 303 might be used, for example, when coating stent 206 with a composition of ethylene vinyl alcohol copolymer with dimethyl sulfoxide, as will be described in greater detail in the example below. In alternative embodiments, no heating act is used, and stent 206 may be implanted immediately after centrifugation act 302. The use of a heating step and the parameters of such a step will vary with the application.

In act 304, it is determined whether one or more additional layers of coating substance is to be applied to stent 206. If so, the process returns to act 301, and another layer of coating substance is applied. Multiple layers of coating substance may be applied to produce a more uniform coating with fewer defects. Each layer can be formed very thin and uniform, and subsequent layers can be added to increase the overall loading onto stent 206. Moreover, the use of multiple layers can provide enhanced control over the release rate of the coating. Finally, when the desired number of layers have been applied, the process is completed at act 305, and stent 206 may be packaged for delivery or immediately implanted into a patient's body using techniques well-known to those of ordinary skill in the art.

In another embodiment shown in FIG. 4, act 401 involves applying a first coating substance to a portion of stent 206. As previously described, the coating may be applied by injecting, spraying or immersing stent 206 with an aqueous coating substance using techniques similar to those described in the background section above. In act 402, the still-wet stent 206 is inserted onto mandrel 204 in centrifuge container 112 such that mandrel 204 extends through the hollow interior of stent 206. Centrifuge container 112 is then inserted into chamber 110 of centrifuge system 100 (FIG. 1), and centrifuge system 100 is used to rotate stent 206 about axis 106 at high speeds.

The rotation of chambers 110 at high speeds creates a centrifugal force upon the coating substance that previously was applied to the surface of stent 206. Centrifugal force causes excess accumulations of coating substance, particularly the portions entrained between the struts of stent 206, to be more evenly redistributed over stent 206. Redistribution of the coating substance over the surface of stent 206 provides a more uniform coating free of webbing.

The centrifugation of stent 206 may result in some excess coating substance being removed from the surface of stent 206. Drainage openings 210 are provided in support 202 so that the runoff coating substance can flow from the upper portion of centrifuge container 112 into runoff reservoir 208. The channeling of runoff coating substance into runoff reservoir 208 prevents the coating substance from accumulating at the bottom end 212 of stent 206, which could lead to a non-uniform coating. This runoff coating substance can be recovered from runoff reservoir 208 and reused to coat additional stents 206. The recycling of the coating substance can produce significant cost savings when an expensive therapeutic agent is being used.

In act 403, coated, centrifuged stent 206 is immediately placed into a conventional oven for heating. In alternative embodiments, no heating act is used, and stent 206 may be implanted immediately after centrifugation act 302. The use of a heating step and the parameters of such a step will vary with the application.

In act 404, whether additional coating substance is to be applied to a portion or portions of stent 206 is determined. If so, the process returns to act 401, and additional coating substance is applied to a portion or portions of stent 206. Each portion of stent 206 can be covered in a different coating substance. For example, in one embodiment a first end of stent 206 is dipped into a first coating substance. Stent 206 is then centrifuged to provide an even coating at the first end. Next, the second end of stent 206 is dipped into a second coating substance, and stent 206 is again centrifuged to provide an even coating at the second end.

In another embodiment, a first coating substance is applied to an interior portion or surface of stent 206 and a second coating substance is applied to an exterior surface or portion of stent 206. In addition to a general stent structure, the following coating configuration also applies to other devices, including a stent graft or sheath covered stent. Further, the structural configuration of the stent graft or sheath covered stent also prevents the two coating substances from intermixing. For this embodiment, the stent 206 is inserted onto a mandrel in the centrifuge container and a volume or drop (i.e., approximately 20 microliters) of first coating substance is dripped into the interior portion of the stent. As such, the substance generally coats the interior portion as the viscous substance drips through the stent. Second and third drops of the first coating substance are also applied in a similar manner, for a total of approximately 60 microliters of substance coating the interior portion of the stent. The stent is then centrifuged and dried in an oven at approximately 50° C. for 5 hours. Approximately 60 microliters are similarly applied to the exterior of the stent, centrifuged and dried according to the above procedure to produce an evenly interior and exterior coated stent.

When the desired number of layers have been applied, the process is completed at act 405, and stent 206 may be packaged for delivery or immediately implanted into a patient's body using techniques well-known to those of ordinary skill in the art.

The application of one or more coating substances to different portions of the stent or graft precludes potential physical and/or chemical interactions from occurring between multiple substances. In addition, this coating technique also allows variable layers of the same or different substances to be applied to specific portions of the stent, thereby providing enhanced site-specific treatment of various disease states and/or conditions.

For example, stents uniformly coated with radioactive materials that limit cell proliferation have been used to treat restenosis. However, one side effect of this treatment method is the occurrence of a "candy-wrapper" effect at the treatment site. In general, the candy-wrapper effect is characterized by enhanced restenosis at the ends or edges of the radioactive stent that cause the ends of the stent to twist and contract in a radially inward direction. The abrupt change in radioactive levels at the edges of the stent, e.g. between tissue contacting the radioactive stent versus tissue not contacting the stent, is thought to further stimulate the proliferation of smooth muscle cells at these sites.

One method of mitigating this effect is to apply variable layers of radioactive material along the surface of the stent. In general, the level or amount of radiation at a tissue site is proportional to the number of layers of radioactive substance applied to the corresponding portion of the stent. As such, gradually decreasing the number of radioactive material layers towards the ends of the stent provides a smooth transition in radiation amounts between adjacent tissue cells. For example, for material delivering a radiation dosage of 10–100 gray (Gy) approximately 1 to 5 layers of material are applied to the central portion of the stent. Successively decreasing numbers of layers of the radioactive material are applied to the stent, terminating at the end or edge portions of the stent having only 1 to 2 layers of material. Other radioactive materials and layer variations, though not expressly disclosed, may also be used. This, in turn, inhibits cell stimulation and proliferation in tissue contacting the stent surface and portions of surrounding tissues, thereby preventing the occurrence of the candy-wrapper effect.

Alternatively, materials having different levels of radioactive substances may also be used to counteract the candy wrapper effect. For this embodiment, materials containing higher levels or dosages of radioactive substances are applied in a single layer near the central portion of the stent. Likewise, single layers of lower radioactive substances, whereby the radioactive levels are successively decreasing in the direction away from the central portion of the stent, are also applied to the surface of the stent. Exemplary dosage ranges of radioactive substances, whereby the high dosage range represents materials applied to the central portion of the stent and the low dosage range represents materials applied to the edge sections of the stent, are 50Gy to 100Gy and 10Gy to 30Gy, respectively. As described above, the stent configuration prevents cell stimulation and proliferation in tissue contacting the stent and, also, in surrounding tissues.

In yet another embodiment, the edges of the stent contain increased levels of radioactivity compared to the central portion of the stent. The dosage of radioactivity at the edges of the stent is configured to inhibit stimulation and proliferation of surrounding cells. As such, the radioactive material arrests cell division not only at the edges of the stent, but also in the surrounding tissue. In general, the level of radioactive substance applied to the end portions is approximately 500% to 1,000% greater than the level of radioactive substance applied to the central portion of the stent. As such, the increased dosage of radioactive material applied to the end portions of the stent inhibits the occurrence of the candy wrapper effect.

Grafts and stent coverings may include a large number of interstices, which cause these devices to have a generally permeable characteristic. In accordance with various embodiments of the present invention, permeable grafts and stent coverings can be coated with a coating substance, such as those described above, and then placed into a centrifuge for centrifugation. The centrifugation process provides improved perfusion of the coating substance through the interstices of the graft or stent covering, particularly when the devices are formed of a highly hydrophobic material.

In another embodiment, a process for applying a hydrogel coating to a graft or stent covering is provided. When applying a hydrogel coating, a coating substance containing at least one crosslinkable pre-polymer and a first fluid in which the pre-polymer is soluble is prepared. The pre-polymer should be in true solution, saturated, or supersaturated with the first fluid. Exemplary crosslinkable pre-polymers include, but are not limited to, polyethylene glycol (PEG) diacrylate, hyaluronic, and pluronic. The concentration of pre-polymer in the composition should be selected such that it is high enough to ensure effective crosslinking of the pre-polymer since a solution too dilute may not form a crosslinked hydrogel. An implantable device may then be dipped into this pre-polymer coating substance. Alternatively, prior to application of the pre-polymer, the implantable device may be perfused with a low surface energy solvent such as, for example, acetone or ethanol, which effectuates improved perfusion of the pre-polymer solution through the interstices of the implantable device.

After the implantable device is dipped into the pre-polymer solution, the implantable device is placed in a centrifuge container and loaded into a centrifuge system, similar to the centrifuge container 112 and centrifuge system 100 described above. Centrifuging the coated implantable device spreads the viscous pre-polymer solution evenly across the surface of the implantable device and into the interstices or crevices therein.

The pre-polymer is cured to form a hydrogel coating on the implantable device. Curing may be accomplished photochemically using ultraviolet or visible irradiation and a photoinitiator, thermally, or by moisture curing at room temperature. The practice of these and other suitable curing procedures is well known to those of ordinary skill in the art.

In yet another embodiment, the coating method of the present invention can be used to provide a physician with greater flexibility in selecting a desired coating substance for use with a particular patient. Conventionally, stents are coated by either the stent manufacturer or a third party prior to delivering the stent to a physician for implantation into a patient. In accordance with the present invention, a physician can apply a coating on a bare stent, centrifuge the stent using a small, portable centrifuge device, and implant the freshly-prepared stent in a patient's body. This enables the physician to precisely select the composition of the coating substance applied to the stent. In addition, because the stent can be locally coated and then immediately implanted by the physician after coating, perishable or environmentally-sensitive materials may be used to coat the stent.

EXAMPLE 1

An ACS Duet® stainless steel stent 206, produced by Guidant Corp. of Indianapolis, Ind., is partially dipped or immersed (e.g., for a few seconds or up to 20 seconds or more) in a coating substance composed of BioSpan® (a polyurethane) and Trapidil (i.e., triazolopyrimidine, an antiplatelet) in a 3:1 ratio. The stent 206 is then immediately mounted into a centrifuge container 112, as described above with respect to FIGS. 1–4. The centrifuge container 112 is inserted into chamber 110 and rotated for 30 seconds at 2500 rpm.

The stent 206 is then removed from the centrifuge container 112, placed on a mandrel, and loaded into a Blue M model vacuum convection oven from the Blue M Electric company of Watertown, Wis., for 24 hours at a temperature of 50° C. The heating causes the coating substance to fully dry, leaving a thin coating of BioSpan® and Trapidil on a portion of the stent.

Next, the immersion, centrifugation, and heating acts are repeated on the uncoated portion of the stent 206. For these subsequent processes, the uncoated portion of the stent is dipped or immersed in Duraflo® heparin solution (manufactured by Baxter, Deerfield, Ill.; referenced herein after as "Duraflo®").

The above-described process results in a physically separated, selective coating of two different biologically active agents on the stent.

EXAMPLE 2

Multi-Link Duet™ stents, produced by Guidant Corp. of Indianapolis, Ind., are cleaned in an ultrasonic bath of isopropyl alcohol for 20 minutes, then air dried. An ethylene vinyl alcohol (EVAL) stock solution is made having an EVAL:DMSO:THF w/w ratio of 1:2:1.5. The mixture is placed in a warm water shaker bath at 60° C. for 12 hours. The solution is mixed, then cooled to room temperature. A 9% by weight Dexamethasone solution is formulated as follows: 0.91 grams of the EVAL:DMSO:THF solution is mixed with 0.09 grams of Dexamethasone. The cleaned Multi-Link Duet™ stents are mounted in a makeshift holder placed within ependorf tubes. One half of the stent is dipped in the EVAL-Dexamethasone solution and transferred to the ependorf tube. The dipped end is vertically lower and resting on the holder in the tube. The tube is then centrifuged at 3000 rpm for 60 seconds. The half-coated stent is dried for 2 hours in a vacuum oven at 50° C. Following drying, the clean half of the stent is dipped in Duraflo® (organic soluble heparin) made at 10% w/w in Freon. The coating process is repeated. The final coating configuration results in a one-half Dexamethasone and other one-half Heparin-coated stent.

EXAMPLE 3

Multi-Link Duet™ stents are cleaned in an ultrasonic bath of isopropyl alcohol for 20 minutes, then air-dried. An ethylene vinyl alcohol (EVAL) stock solution is made having an EVAL:DMSO:THF w/w ratio of 1:2:1.5. The mixture is placed in a warm water shaker bath at 60° C. for 12 hours. The solution is mixed, then cooled to room temperature. A 5% by weight Actinomycin-D (Ac-D) solution is formulated as follows: 0.95 grams of the EVAL:DMSO:THF solution is mixed with 0.05 grams of AcD. The cleaned Multi-Link Duet™ stents are mounted in a makeshift holder placed within ependorf tubes. One half of the stent is dipped in the EVALA-cD solution and transferred to the ependorf tube. The dipped end is vertically lower and resting on the holder in the tube. The tube is then centrifuged at 3000 rpm for 60 seconds. The half-coated stent is dried for 2 hours in a vacuum oven at 50° C. Following drying, the clean half of the stent is dipped in Duraflo® (organic soluble heparin) made at 10% w/w in Freon. The coating process is repeated. The final coating configuration results in a one-half AcD and one-half Heparin-coated stent.

EXAMPLE 4

Multi-Link Duet™ stents are patterned with microdepots on the outer diameter of the stents. Microdepot stents are cleaned in an ultrasonic bath of isopropyl alcohol for 20 minutes, then air dried. A 10% AcD stock solution is made having an AcD:THF w/w ratio of 10:90. A 10% Dexamethasone stock solution is made having a Dexamethasone-:THF w/w ratio of 10:90. The cleaned Multi-Link Duet™ stents are mounted in a makeshift holder placed within ependorf tubes. One half of the stent is dipped in the AcD solution and is transferred to the ependorf tube. The dipped end is vertically lower and is resting on the holder in the tube. The tube is then centrifuged at 2000 rpm for 60 sec. The half-coated stent is dried for 1 hour in a vacuum oven at 30° C., Following drying, the clean half of the stent is dipped in the Dexamethasone solution. The coating process is repeated. The drug loaded stents are then coated with Duraflo® solution by spraying a solution of Duraflo® as described in previous embodiments. The final coating configuration results in a one-half AcD and other one-half Dexamethasone coated microdepot stent that is topcoated with Heparin.

The rotational speed during centrifugation can be varied. Higher RPM values may provide improved uniformity and a reduction in defects. However, lower RPM values may improve solid uptake, i.e., the total loading of the coating substance onto stent 206. The solid uptake is calculated by measuring the initial weight of stent 206, and then measuring the weight after the loading and centrifugation acts. Increasing the total centrifugation time may also improve the uniformity and reduce defects in the coating. Accordingly, practitioners should tailor the process to the particular application.

Various embodiments of the described method enable highly viscous materials to be coated onto implantable devices. Viscous materials are not usually amenable to conventional coating methods such as dipping or spraying, because of the viscous material's propensity to accumulate in an uneven layer. However, the addition of a centrifugation step after dipping the implantable device in the viscous coating material can transform the uneven masses into a smooth, even coating.

Embodiments of the method also enable uniform coatings to be applied to implantable devices with improved repeatability, thereby improving coating uniformity between batches of implantable devices. With conventional manually-applied spray-coating techniques, operator error or inconsistency may result in different coating thicknesses between batches of stents. The centrifugation processes can reduce unwanted gross deposition of coating substances and enable high reproducibility of the coating quality.

Embodiments of the method also enable multiple stents to be processed simultaneously. Unlike manually-applied airbrush coating methods, in which stents are coated individually or in small groups, large batches of stents can be simultaneously immersed in the coating solution, simultaneously rotated in the centrifuge device, and simultaneously heated in an oven, thereby increasing throughput.

Embodiments of the method also may improve operator safety when coating implantable devices with hazardous materials. It is generally not desirable to spray coat an implantable device with toxic or radioactive coating substances, because of the increased exposure of the operator to the airborne hazardous coating substance. Dipping and centrifuging the implantable device as described above can decrease the amount of handling required for the coating process, resulting in reduced environmental contamination.

Embodiments of the method may also mitigate defects due to handling of the implantable device. In conventional spray processes, the implantable device is held aloft using one or two clamps or fixtures while the coating substance is sprayed onto the device. The point where these clamps contact the device may be masked from receiving the spray, resulting in defects in the coating. In contrast, the centrifuge container 112 has minimal contact with the implantable device during the centrifuge process.

In general, the coating substance of the various embodiments can have a viscosity within the range of about 0.5 cp to 1,000 cp (centipoise) (whereby 1 cp is approximately equal to the viscosity of water at 20° C.). As such, 0.5 cp approximately represents a very thin substance, 100 cp approximately represents, for example, a light oil, and 1,000 cp approximately represents a thick, viscous substance. Further, the relationship between the centrifugal force of the centrifuge or similar device and the viscosity of the coating substance can be approximately represented by the following equation:

$$U \sim (g + r * f^2)/k*m$$

Where: U=velocity
  g=gravitational acceleration
  r=average distance*$4\pi^2$
  f=rpm
  k=surface area to volume ratio (and other geometric constants/parameters)
  m=kinetic viscosity In addition to the above, the viscosity of the coating substance is also dependent on the type of polymer and concentration of polymer contained in the coating substance.

The above embodiments only illustrate the principles of this invention and are not intended to limit the invention to the particular embodiments described. For example, the heating to evaporate the solvent material may be omitted, and other embodiments utilizing centrifugation coating methods can be used in combination with other acts in different processes which do not require active heating. These and various other adaptations and combinations of features of the embodiments disclosed are within the scope of the invention, as defined by the following claims.

We claim:

1. A method of coating a tubular implantable medical device, comprising:
   applying a first coating substance to an area along a first length of the outer surface of the device;
   rotating the device about an axis of rotation for distributing the first coating substance along the first length;
   allowing the first coating substance to solidify to form a first coating on the first length;
   applying a second coating substance to an area along a second length of the outer surface of the device, wherein the second length does not include the first coating;
   rotating the device about an axis of rotation for distributing the second coating substance along the second length; and
   allowing the second coating substance to solidify to form a second coating on the second length.

2. The method of claim 1, wherein the first coating includes approximately the entire outer surface of at least the first half of the length of the device and the second coating includes approximately the entire remaining outer surface.

3. The method of claim 1, wherein the first coating substance is applied by dipping the first end of the device in the first coating substance.

4. The method of claim 1, wherein the second coating substance is applied by dipping the second end of the device, up to at least the first length that is covered with the first coating, in the second coating substance.

5. The method of claim 1, wherein the first and second coating substances are solidified by exposing the device to heat.

6. The method of claim 1, wherein the device is a stent, a graft, a stent-graft, or a cover for the same.

7. The method of claim 1, wherein the device is rotated by a centrifugation device.

8. The method of claim 1, wherein the device is positioned at a distance away from the axis of rotation.

9. The method of claim 1, wherein an axis of the device, extending longitudinally along the center of the device is positioned at a distance from and is generally parallel to the axis of rotation.

10. The method of claim 1, wherein the first coating substance comprises a polymer dissolved in a solvent and optionally a therapeutic substance added thereto.

11. The method of claim 1, wherein the second coating substance comprises a polymer dissolved in a solvent and optionally a therapeutic substance added thereto.

12. A method of manufacturing a drug eluting stent, comprising:
   applying a first composition to a first end of a stent wherein the first composition covers up to a selected length of the stent;
   rotating the stent in a centrifuge device to provide sufficient centrifugal force to distribute the first composition at least along the length of the stent that has been exposed to the first composition;
   allowing the first composition to solidify to form a first coating;
   applying a second composition to a second end of the stent wherein the second composition covers at least a portion of the remaining length of the stent not covered by the first coating;
   rotating the stent in the centrifuge device to provide sufficient centrifugal force to distribute the second composition at least along a portion of the remaining length of the stent; and
   allowing the second composition to solidify to form a second coating on the stent.

13. The method of claim 12, wherein the first or second composition comprises a polymer dissolved in a solvent and optionally a therapeutic substance added thereto.

14. The method of claim 12, wherein the stent is in a generally vertical position in the centrifuge device.

15. A method of coating a tubular implantable medical device, comprising:
   applying a first coating substance to a tubular implantable medical device along a first length of the device;
   rotating the device about an axis of rotation to provide sufficient centrifugal force to distribute the first coating substance along the first length;
   applying a second coating substance to the device along a second length of the device, the second length being free of the first coating substance; and
   rotating the device about an axis of rotation to provide sufficient centrifugal force to distribute the second coating substance along the second length.

16. The method of claim 15, wherein the first and second coating substances comprise different therapeutic substances.

17. The method of claim 15, wherein the first coating substance is applied by dipping the first end of the device in the first coating substance.

18. The method of claim 15, wherein the second coating substance is applied by dipping the second end of the device, up to at least the first length that is covered with the first coating substance, in the second coating substance.

19. The method of claim 15, wherein the device is a stent, a graft, a stent-graft, or a cover for the same.

20. The method of claim 15, wherein the device is rotated by a centrifugation device.

21. The method of claim 15, wherein the device is positioned at a distance away from the axis of rotation.

22. The method of claim 15, wherein an axis of the device, extending longitudinally along the center of the device, is positioned at a distance from and is generally parallel to the axis of rotation.

23. The method of claim 15, wherein the first coating substance comprises a polymer dissolved in a solvent and, optionally a therapeutic substance added thereto.

24. The method of claim 15, wherein the second coating substance comprises a polymer dissolved in a solvent and optionally a therapeutic substance added thereto.

25. A method of coating an implantable medical device, comprising:

applying a first composition to a first end of an implantable medical device wherein the first composition covers up to a selected length of the medical device;

rotating the medical device in a centrifuge device to provide sufficient centrifugal force to distribute the first composition at least along the length of the medical device that has been exposed to the first composition;

applying a second composition to a second end of the medical device wherein the second composition covers at least a portion of the remaining length of the medical device not covered by the first composition;

rotating the medical device in the centrifuge device to provide sufficient centrifugal force to distribute the second composition at least along a portion of the remaining length of the medical device.

26. The method of claim 25, further comprising allowing the first composition to solidify on the medical device to form a first coating and allowing the second composition to solidify on the medical device to form a second coating.

27. The method of claim 26, wherein the first coating includes approximately the entire surface of at least the first half of the length of the medical device and the second coating includes approximately the entire remaining surface.

28. The method of claim 26, wherein the first and second coatings do not overlap.

29. The method of claim 25, wherein the first or second composition includes a therapeutic substance for the treatment of restenosis.

30. The method of claim 25, wherein the medical device is in a generally vertical position in the centrifuge device.

* * * * *